(12) United States Patent
Songer et al.

(10) Patent No.: US 6,395,030 B1
(45) Date of Patent: May 28, 2002

(54) SPINAL FIXATION SYSTEM

(75) Inventors: Matthew N. Songer, Marquette; Jeffrey D. Vlahos, Bruce Crossing; Thomas S. Kilpela, Marquette; Gopal Jayaraman, Houghton, all of MI (US)

(73) Assignees: Michigan Technological University, Houghton; Pioneer Laboratories, Inc., Marquette, both of MI (US)

(*) Notice: Subject to any disclaimer, the term of this patent is extended or adjusted under 35 U.S.C. 154(b) by 0 days.

(21) Appl. No.: 09/561,248

(22) Filed: Apr. 27, 2000

Related U.S. Application Data

(63) Continuation-in-part of application No. 09/099,310, filed on Jun. 18, 1998, now abandoned.

(51) Int. Cl.[7] .................................................. A61F 2/44
(52) U.S. Cl. .................................................. 623/17.11
(58) Field of Search .......................... 623/17.11, 17.15, 623/17.16

(56) References Cited

U.S. PATENT DOCUMENTS

| | | | |
|---|---|---|---|
| 4,289,123 A | 9/1981 | Dunn | |
| 4,401,112 A | 8/1983 | Rezaian | |
| 4,554,914 A | 11/1985 | Kapp et al. | |
| 4,599,086 A | 7/1986 | Doty | |
| 4,636,217 A | 1/1987 | Ogilvie et al. | |
| 4,743,256 A | 5/1988 | Brantigan | 623/17 |
| 4,759,769 A | 7/1988 | Hedman et al. | 623/17 |
| 4,892,545 A | 1/1990 | Day et al. | 623/17 |
| 5,059,193 A | 10/1991 | Kuslich | |
| 5,147,360 A | 9/1992 | Dubousset | |
| 5,147,363 A | 9/1992 | Harle | 606/72 |
| 5,192,327 A | 3/1993 | Brantigan | |
| 5,261,911 A | 11/1993 | Carl | |
| 5,304,210 A | 4/1994 | Crook | 607/51 |
| 5,306,307 A | 4/1994 | Senter et al. | |
| 5,306,309 A | 4/1994 | Wagner et al. | |
| 5,360,430 A | * 11/1994 | Lin | 606/61 |
| 5,425,773 A | 6/1995 | Boyd et al. | |
| 5,458,641 A | 10/1995 | Ramirez Jimenez | 623/17 |
| 5,556,431 A | 9/1996 | Buttner-Janz | |
| 5,591,235 A | 1/1997 | Kuslich | 623/17 |
| 5,603,713 A | 2/1997 | Aust et al. | |
| 5,674,296 A | * 10/1997 | Bryan et al. | 623/17 |
| 5,702,453 A | 12/1997 | Rabbe et al. | 623/17 |
| 5,755,796 A | 5/1998 | Ibo et al. | 623/17 |
| 5,888,223 A | * 3/1999 | Bray, Jr. | 623/17 |
| 5,916,267 A | 6/1999 | Tienboon | 623/17 |

OTHER PUBLICATIONS

Article from Chapter 19/Application of Rezaian Anterior Fixation System by S.M. Rezaian, entitled: "Application of Rezaian Anterior Fixation System for the Management of Fractures of Thoracolumbar Spine", pp. 193–199.

(List continued on next page.)

Primary Examiner—Corrine McDermott
Assistant Examiner—Thomas Barrett
(74) Attorney, Agent, or Firm—Garrettson Ellis Seyfarth Shaw

(57) ABSTRACT

An implantable, spinal, vertebral replacement device comprises a tubular cage for fitting into a space left by a missing vertebral body and for optionally retaining bone graft material. First and second transverse plates are respectively positioned at opposed ends of the tubular cage for supporting the respective cage ends and for pressing a plate face against an adjacent vertebral body in spinal column-supporting relation. The transverse plates are each joined in transverse relation to at least one vertebral attachment plate which, in use, extends generally parallel to the spine. The vertebral attachment plate defines screw holes for screw securance to at least one vertebral body adjacent to the space. Preferably, one or more vertebral attachment plates are connected to the pair of adjacent vertebral bodies that bracket the space left by the missing vertebral body.

30 Claims, 2 Drawing Sheets

OTHER PUBLICATIONS

Article from: AcroMed Surgeon–driven spinal solutions entitled: Thoracolumbar Trauma & Tumor dated Jul. 1995, 12 pages.

Article from: AcroMed The leader in spinal technology entitled: "Kaneda SR (Smooth Rod) Anterior Spinal System, Titanium", 1994 AcroMed Corporation, 6 pages.

Article from: AcroMed The leader in spinal technology entitled: University AM Plate Titanium Anterior System, AcroMed Corporation Sep. 1994, 5 pages.

Article from: 43rd Annual Meeting, Orthopaedic Research Society, Feb. 9–13, 1997, p. 382, entitled: "Comparatvie Kinematics of a collapsible and Rigid Anterior Devices" by Goel et al., Iowa Spine Research Center, University of Iowa.

Article from: SPINE vol. 22, No. 6, pp 686–690, 1997, Lippincott–Raven Publishers, entitled: "Anterolateral Dynamized Instrumentation and Fusion for Unstable Thoracolumbar and Lumbar Burst Fractures" by Carl et al.

SPINE vol. 23, No. 5, pp 543–550, Article entitled: "Stability Potential of Spinal Instrumentations in Tumor Vertebral Body Replacement Surgery" by Vahldiek et al., 1998.

Article by Edmund T. Dombrowski, Jr., MD entitled: "Rezaian Fixator in the Anterior Stabilization of Unstable Spine" from Orthopaedic Review vol. XV, No. 1, Jan., 1986, pp. 30–34.

* cited by examiner

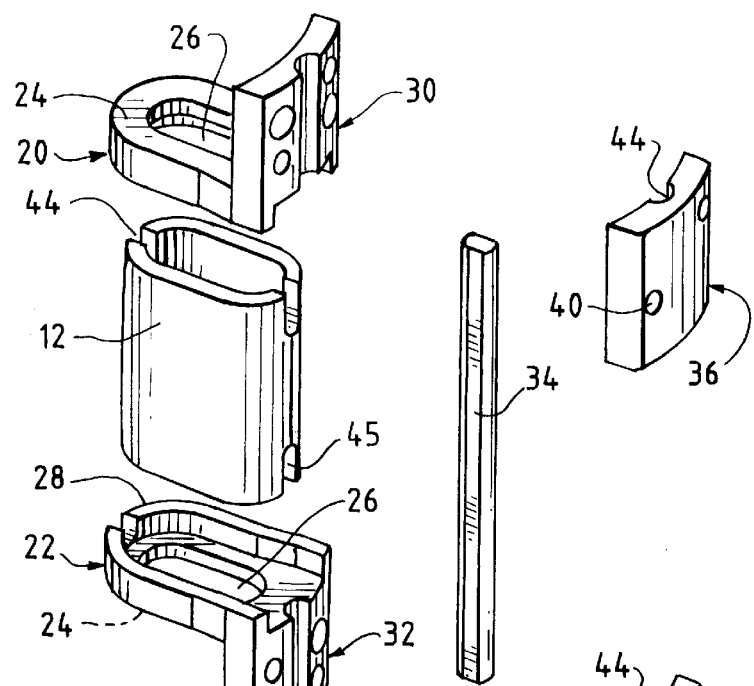
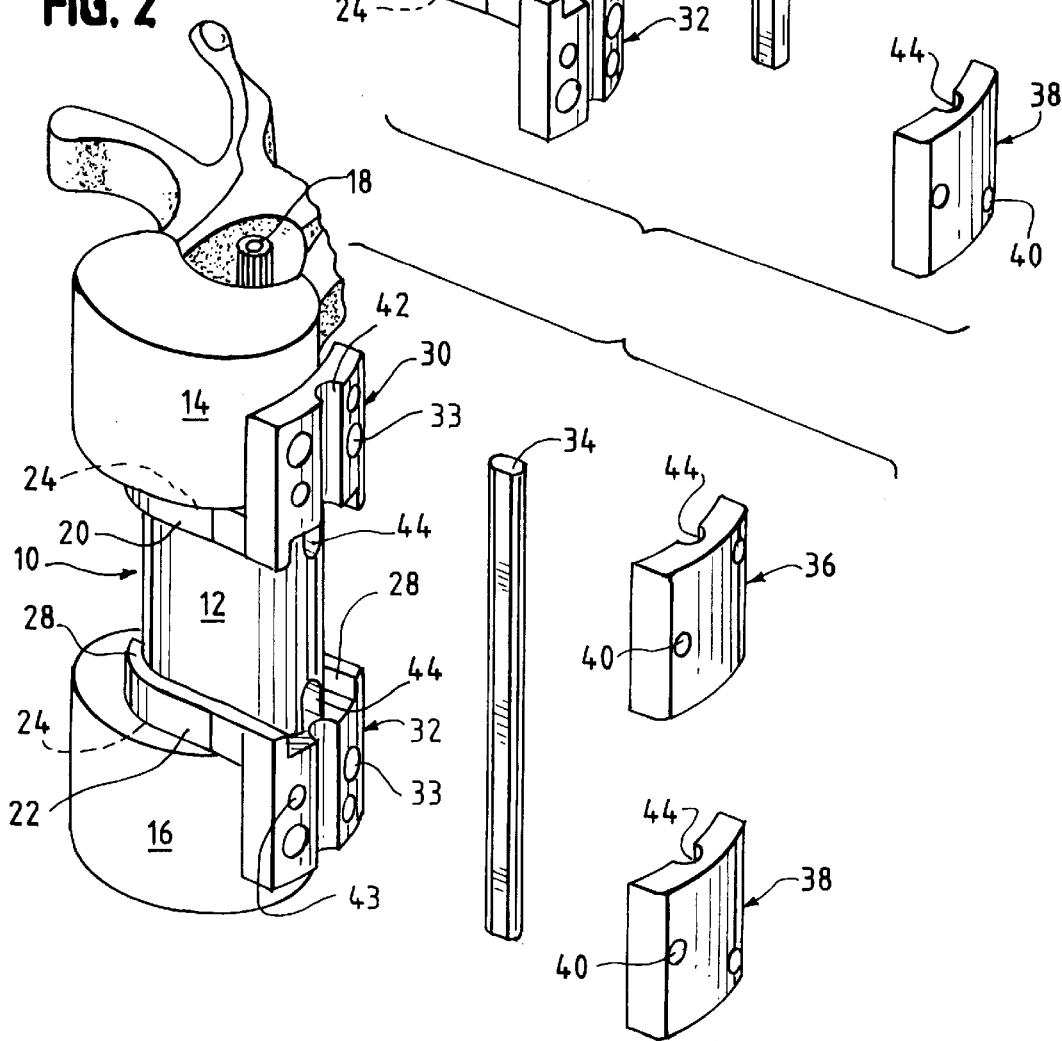

SPINAL FIXATION SYSTEM

CROSS REFERENCE TO RELATED APPLICATIONS

This is a continuation-in-part of Songer et al. U.S. application Ser. No. 09/099,310, filed Jun. 18, 1998 now abandoned.

BACKGROUND OF THE INVENTION

There are various devices and techniques for reconstructing the anterior spinal column in the lumbar or thoracic spine. Specifically, a bone graft may be inserted between the vertebrae. The spine is then fused posteriorly with an implantable instrument of various designs.

However, the bone graft usually was obtained from the fibula or the iliac crest. Problems have arisen with donor site morbidity.

Also, various implantable devices for reconstruction of the spine comprise anterior plate and/or anterior rod systems.

Typically, one of two methods are used to reconstruct the anterior spine. Either an autologous bone graft or an allograft is inserted into the defect, and a plate system is applied to the lateral side of the spine. Alternatively, a tubular "cage" may be inserted between vertebral bodies, and a plate may be applied, extending between intact vertebral bodies on either side of the defect. The cage may be filled with bone graft material such as bone fragments. The cage retains the material in place while the bone graft grows, fusing the two adjacent vertebral bodies.

By this invention, an integral, modular device is provided to replace a vertebral body that has been destroyed or must be removed because of fracture, tumor, infection or the like, while the device of this invention provides a site for an effective bone graft to fuse with intact, adjacent vertebral bodies, with both the device and the optional bone graft extending between the adjacent vertebral bodies and across the original space of the missing vertebral body.

DESCRIPTION OF THE INVENTION

By this invention, an implantable, spinal, vertebral replacement device is provided. The device comprises a tubular cage for fitting into a space of a missing or damaged vertebral body. This tubular cage may be made of titanium, carbon fiber composite, bone, or the like, and can be used if desired to retain bone graft material in a desired position between intact vertebral bodies to form a fusion between the intact vertebral bodies across the site of the missing vertebral body. First and second transverse plates are respectively positioned at opposed ends of the tubular cage for supporting the respective ends of the tubular cage, and for pressing a plate face against an adjacent vertebral body in spinal column-supporting relation.

The transverse plates are each joined in transverse relation to at least one vertebral attachment plate. This latter plate, in use, extends generally parallel to the spine, with the vertebral attachment plate defining screw holes for screw securance to at least one vertebral body adjacent to the space of the missing vertebral body.

Accordingly, by this invention both support and spacing of adjacent vertebral bodies is provided, along with retention and positioning of a tubular cage, which can retain bone graft material for the future growth of a strong bone graft after surgery.

In one embodiment, each transverse plate may be joined to a separate vertebral attachment plate, for attachment of each vertebral attachment plate to a separate, adjacent vertebral body positioned on an opposed side of the space left by the missing vertebral body. In this circumstance, it is preferred for a support rod to extend generally parallel to the spine and to be retained between the vertebral attachment plates. The rod may be retained at each vertebral attachment plate by a frictional pressure retention of a cover plate which is carried, one on each vertebral attachment plate, in a position to frictionally press the rod against the vertebral attachment plate at a retention site thereof, and also cover the screw holes for screw securance to a vertebral body, and to also cover the screws occupying those holes. Thus, backing out of the screws in the holes after implantation of the device can be suppressed by the presence of such a cover plate.

It is also preferred for the rod to be of non-circular cross section, being retained between respective vertebral attachment plates and cover plates while residing in appropriately shaped grooves of said plates.

As an alternate design, the spinal replacement device of this invention may utilize a single vertebral attachment plate, to which both transverse plates are attached, with the vertebral attachment plate having screw holes for attachment to both of the adjacent, vertebral bodies.

As a further feature of this invention, the transverse plates may each have a peripheral, upstanding wall to surround and retain a respective supported end of the cage to prevent lateral cage movement. The peripheral, upstanding wall and cage are respectively dimensioned to preferably cause tight retention of the cage. The peripheral upstanding wall is preferably open at one end of the transverse plate, preferably the end facing the vertebral attachment plate, to receive the cage with lateral motion relative to the spinal column, this specific embodiment is particularly used with the system having the pair of vertebral attachment plates. Such a system can be used with cages of varying length, which slide into engagement with the peripheral, upstanding walls of the transverse plates.

Preferably, each transverse wall has a roughened face that faces the adjacent, intact vertebral body against which it presses in use. The roughened face may comprise a titanium mesh coating secured to the face of the plate that engages an end of the adjacent vertebral body, or it may be prepared by a variety of other, known techniques.

Also, each transverse plate preferably defines a central aperture, so that communication is available between the intact vertebral bodies and the bone graft material within the cage.

Some adjustability can be provided to the embodiment having a single vertebral attachment plate by providing the transverse plates with a hinged connection with the vertebral attachment plate, or even a frictional, spring-pinching connection between two flat surfaces of each transverse plate, respectively engaging opposed side surfaces of the vertebral attachment plate. Additionally, a bracket or strap may extend across an open end of the vertebral attachment plate with an aperture, for later application if desired after the cage has been positioned in the desired, surgical position, for better retention of each transverse plate with the vertebral attachment plate.

Preferably, the cage defines a slot at at least one end thereof, which slot is proportioned to receive a surgical distractor, for use during insertion of the cage into a position between the vertebral bodies.

Also, the cage may be elongated in one transverse dimension relative to its other transverse dimension, with the long dimension generally extending from side to side of the spine.

Accordingly, by the use of the above principles, a spinal replacement device is provided which can exhibit a unique combination of advantages, including a solid, firm retention of the entire system properly positioned in the spine, coupled with the facility to retain bone graft material in a position where growth can take place so that, after convalescence, the patient is less dependent upon the non-living implant, and more dependent on a more natural regrowth of bone in the spine.

DESCRIPTION OF THE DRAWINGS

In the drawings, FIG. 1 is an exploded, perspective view of the components of one embodiment of the spinal replacement device of this invention;

FIG. 2 is a perspective, partially assembled view of the spinal replacement device of FIG. 1, shown in the process of implantation in the spine to replace a missing vertebral body;

DESCRIPTION OF SPECIFIC EMBODIMENTS

Figure 3:
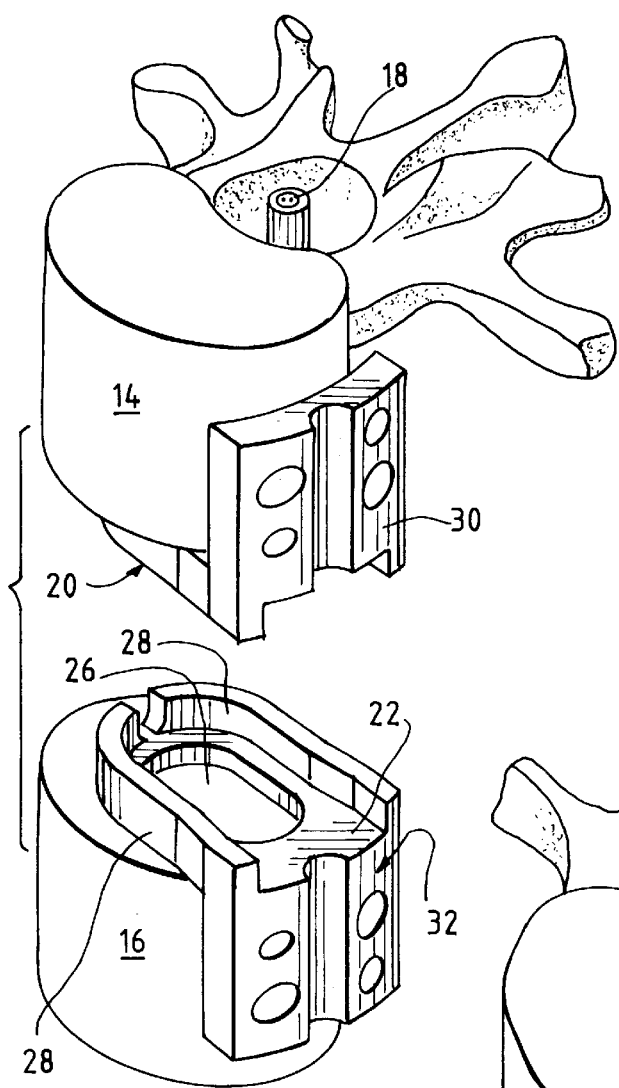
FIG. 3 is an enlarged, perspective view, with the cage deleted, of a portion of the system of FIG. 2, showing more details.

Referring to FIGS. 1–3, an implantable spinal vertebral replacement device is shown. Specifically, device 10 comprises a tubular cage 12 of oval cross section and made for example of titanium or a carbon fiber composite. Alternatively, cage 12 may be made of a length of hollow bone typically having noncircular ends, cut to fit, and having a lumen that extends from end to end of the bone. Tubular cage 12 fits into the space which is left by a missing vertebral body which was either destroyed or had to be surgically removed, positioned between a pair of adjacent, intact vertebral bodies 14, 16 is as shown particularly in FIG. 2. It can be seen that the major transverse cross sectional axis of oval tubular cage 12 preferably extends from side to side of the spine comprising vertebra 14, 16. Cage 12 is positioned anterior to the spinal cord 18.

Cage 12 may be filled with bone fragments or other bone graft material so that, ultimately, an intact bone graft will be formed, extending between intact vertebra 14, 16.

First and second transverse plates 20, 22 are respectively positioned at opposed ends of tubular cage 12, for supporting the respective cage ends and for pressing a face 24 against an adjacent vertebral body 14 or 16 in spinal column-supporting relation. Transverse plates 20, 22 also define an aperture 26, but, typically, the face 24 that presses against the intact, vertebral bodies 14, 16 has more area than the area of each end of cage 12, so that a greater surface area pressing against each vertebral body 14, 16 is provided than would be provided by the mere presence of cage 12.

Also, transverse plates 22, 24 define a peripheral, upstanding wall 28, being dimensioned to cause tight retention of cage 12. Typically, wall 28 is open at one end of each transverse plate to receive the cage with lateral motion (relative to the spinal column). For example, in FIG. 2 it can be seen how cage 12 may enter the area circumscribed by upstanding walls 28 by advancement of transverse plates approximately from the right toward the cage, or by advancement of cage 12 toward the left into engagement with transverse plates 20, 22.

Transverse plates 20, 22 are each joined in transverse relation to at least one vertebral attachment plate. In the embodiment of FIGS. 1–3, a pair of such vertebral attachment plates 30, 32 are used. As shown, vertebral attachment plates 30, 32 extend generally parallel to the spine i.e. generally parallel to the line of vertebra 14, 16, being integrally secured in this embodiment in transverse relation, each to a separate transverse plate 20, 22. Also, each vertebral attachment plate 30, 32 defines first screw holes 33 for screw securance to one of the respective vertebral bodies 14, 16, as shown particularly in FIG. 2, for securance of the spinal vertebral replacement device in position.

In this embodiment, a rod 34 extends generally parallel to the spine and is retained between vertical attachment plates 30, 32 with a frictional pressure retention provided by cover plates 36, 38. Cover plates 36, 38 have screw holes 40 which mate with second screw holes 43 on the vertebral attachment plates 30, 32, for firm pressure attachment to provide a frictional pressure retention seal of rod 34 in the desired position. Also, cover plates 36, 38 serve to restrict and prevent unintended back-out of the bone screws from their retained position within screw holes 33 of the respective vertebral attachment plates 30, 32. Appropriate grooves 42, 44 are respectively provided in the vertebral attachment plates 30, 32 and the cover plates 36, 38 to appropriately receive rod 34.

Rod 34 may be cylindrical, but is preferably of non-circular cross section, to raise the torque resistance of the rod. For example, rod 34 may be of rectangular cross section with the major axis of the rectangle extending transversely from side-to-side of the spine in a direction generally parallel to the major cross-sectional axis of cage 12.

Cage 12 may define an end aperture 45 at each end on the long axis thereof, to provide access for a distractor tool, used in the surgical installation of the system.

Thus, an implantable anterial spinal fixator is provided, in which one or more vertebrae can be replaced with the device of this invention. The device firmly maintains the spacing of missing vertebrae, and also provides the capability for the firm retention and growth of a bone graft, to restore to the spine a more natural, strong regrowth of bone. The system is very flexible for use, and is capable of dimensional variations, for example by the use of varying lengths of the cage 12. If desired, transverse plates 20, 22 may be connected to vertebral attachment plates 30, 32 by a hinge, which provides added dimensional tolerance capability to the system.

Figure 4:
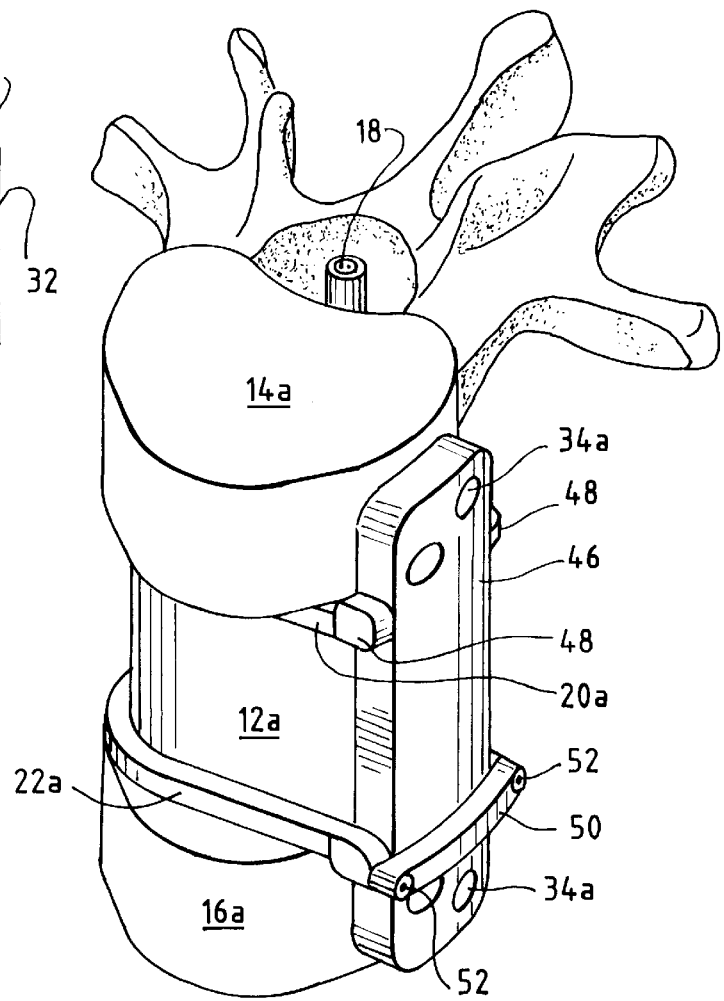
FIG. 4 is a perspective view showing a modified embodiment of the invention in fully implanted form in the spine, replacing a missing vertebral body.

Referring to FIG. 4, another embodiment of the implantable spinal vertebral replacement device of this invention is shown, with the device being shown to be implanted on the spine.

As before, a pair of first and second transverse plates 20a, 22a engage the ends of a tubular cage 12a, and also press with their other faces against intact adjacent vertebral bodies 14a, 16a, all in a manner similar to the previous embodiment.

Transverse plates 20a, 22a each engage a single vertebral attachment plate 46, instead of a pair of vertebral attachment plates as in the last embodiment. Vertebral attachment plate 46 extends basically parallel to the spine as in the previous embodiment, and has pairs of bone screw attachment holes 34a for attachment at the respective ends of vertebral attachment plate 46 to intact, adjacent vertebral bodies 14a, 16a.

Two different modes of attachment for the transverse plates 20a, 22a and the vertebral attachment plate 46 are shown. Transverse plate 20a simply connects in a pressure connection to opposed edges of vertebral attachment plate 46 as shown. Particularly, the ends 48 of plate 20*a* press against vertebral attachment plate 46 with spring pressure. Thus, plate 20*a* can slide up and down the vertebral attachment plate 46 as may be desired for best positioning.

Alternatively, as shown with respect to transverse plate 22*a*, the same spring pressure attachment to vertebral attachment plate 46 may be used, but with a strap 50 extending across the ends of transverse plate 22*a*, with retention screws 52 being used to hold strap 50 and plate 22*a* together. Thus cage 12*a* is strongly held in a desired lateral position by the secured plate 22*a*.

As a further alternative, a cover plate similar to cover plate 38 may be used instead of strap 50 by the simple expedient of providing an enlarged, central section to strap 50 to cover the respective end of vertebral attachment plate 46. Thus, screw holes 34*a* may be covered to prevent accidental, unintended back-out of the bone retention screws, in a manner similar to the previous embodiment.

Typically, the same design for retention will be used at each end of vertebral attachment plate 46, with the different retention systems here being shown for purposes of illustration.

Transverse plate 22*a* can also slide up and down the vertebral attachment plate to a desired position until tightly secured, so that the system of this invention has very substantial dimensional tolerance, and thus can be used with a variety of patients.

The above has been offered for illustrative purposes only, and is not intended to limit the scope of the invention of this application, which is as defined in the claims below.

That which is claimed:

1. An implantable spinal vertebral replacement device, which comprises: a tubular cage of noncircular cross-section at respective ends thereof, for fitting into a space of a missing or damaged vertebral body; and first and second transverse plates, at least one said plate being separate from said tubular cage, said plates being respectively positioned at opposed ends of the tubular cage in a position supporting the respective cage ends while preventing cage axial rotation, and for pressing a plate face against an adjacent vertebral body in spinal column-supporting relation, said transverse plates each defining a central aperture, said transverse plates each being joined in transverse relation to at least one vertebral attachment plate which, in use, extends generally parallel to the spine, said vertebral attachment plate defining screw holes for screw securance to at least one vertebral body adjacent to said space whereby a central, open space extends between the apertures of said first and second plates and through said cage to facilitate bone growth between said adjacent vertebral bodies through said cage, said transverse plates each having a peripheral, upstanding wall to at least partially surround and retain a respective, supported end of said cage to prevent cage movement.

2. The spinal replacement device of claim 1 in which each transverse plate is joined to a separate one of a pair of vertebral attachment plates, for attachment of each vertebral attachment plate to separate, adjacent vertebral bodies positioned on opposed sides of said space, and a rod extending generally parallel to the spine and retained between said vertebral attachment plates.

3. The spinal replacement device of claim 2 in which said rod is of non-circular cross-section.

4. The spinal replacement device of claim 1 in which both transverse plates are attached to the same vertebral attachment plate, said vertebral attachment plate having screw holes for attachment to a pair of said adjacent vertebral bodies.

5. The spinal replacement device of claim 1 in which at least one cover plate is carried on said vertebral attachment plate in a position to cover said screw holes and screws occupying said holes.

6. The spinal replacement device of claim 5 in which a portion of the cover plate periphery matches and lies against a portion of the periphery of the vertebral attachment plate when occupying said position.

7. The spinal replacement device of claim 1 in which said cage comprises a bone having ends of non-circular cross section which are secured in said transverse plates, and a lumen extending therethrough from end to end.

8. The spinal replacement device of claim 1 in which said peripheral, upstanding walls and cage are dimensioned to cause tight retention of said cage, said wall being open at one lateral end of said transverse plate to receive said cage with lateral motion relative to the spinal column.

9. The spinal replacement device of claim 1 in which said transverse plates are joined in vertically hinged relation to said vertebral plate.

10. The spinal replacement device of claim 1 in which each transverse plate defines a central aperture.

11. The spinal replacement device of claim 1 in which each transverse plate has a roughened face that faces the adjacent vertebral body.

12. The spinal replacement device of claim 1 in which said cage defines a slot at at least one end thereof proportioned to receive a surgical distractor, for use during insertion of the case into a position between vertebral bodies.

13. The spinal replacement device of claim 12 which said cage is elongated in one transverse dimension relative to the other transverse dimension.

14. The spinal replacement device of claim 1 in which said cage is elongated in one transverse dimension relative to the other transverse dimension.

15. An implantable spinal vertibral replacement device, which comprises: a tubular cage for fitting into a space left by a missing vertebral body;

first and second transverse plates respectively positioned at opposed ends of the tubular cage and abutting the respective cage ends, for pressing a plate face against an adjacent vertebral body in spinal column-supporting relation, said cage being of non-circular cross section at respective ends thereof, said transverse plates each being joined in transverse relation to one of a pair of vertebral attachment plates which in use extend generally parallel to the spine, said vertebral attachment plates each defining screw holes for screw securance to a vertebral body adjacent to said space, each transverse plate being joined to a separate vertebral attachment plate, for attachment of each vertebral attachment plate to a separate, adjacent vertebral body positioned on opposed sides of said space, at least one of said transverse plates being separate from said tubular cage, and a rod extending generally parallel to the spine and retained between said vertebral attachment plates; and cover plates, carried on each vertebral attachment plate in a position to cover said screw holes with bone screws occupying said holes, said cover plates also frictionally retaining said rod by pressure against said vertebral attachment plates, said transverse plates each having a peripheral, upstanding wall to at least partially surround and retain a respective, supported end of said cage to prevent lateral cage movement and cage rotation.

16. The spinal replacement device of claim 15 in which each transverse plate defines a central aperture to facilitate bone growth between said adjacent vertebral bodies through said cage.

17. The spinal replacement device of claim 15 in which said cage comprises a bone having ends of non-circular cross section which are secured in said transverse plates; and a lumen extending therethrough from end to end.

18. The spinal replacement device of claim 17 in which said peripheral, upstanding wall and cage are dimensioned to cause tight retention of said cage, said wall being open at one lateral end of said transverse plate to receive said cage with lateral motion relative to the spinal column.

19. The spinal replacement device of claim 18 in which each cage defines a slot at at least one end thereof proportioned to receive a surgical distractor, for use during insertion of the cage into a position between vertebral bodies.

20. The spinal replacement device of claim 19 in which said cage is elongated in one transverse dimension relative to the other transverse dimension.

21. The spinal replacement device of claim 18 in which said cage defines a slot at at least one end thereof proportioned to receive a surgical distractor, for use during insertion of the cage into a position between vertebral bodies.

22. The spinal replacement device of claim 21 in which said cage is elongated in one transverse dimension relative to the other transverse dimension.

23. The spinal replacement device of claim 15 in which said cover plate is connected by screw attached to said transverse plate.

24. An implantable spinal vertebral replacement device, which comprises: a tubular cage for fitting into a space left by a missing vertebral body;

first and second transverse plates respectively positioned at opposed ends of the tubular cage for supporting the respective cage ends and for pressing a plate face against an adjacent vertebral body in spinal column-supporting relation, said tubular cage being of non-circular cross section at respective ends thereof, said transverse plates being each joined in transverse relation to a single vertebral attachment plate which, in use, extends generally parallel to the spine, said vertebral attachment plate defining screw holes for screw securance to a pair of vertebral bodies that bracket and are adjacent to said space left by the missing vertebral body, said transverse plates each having a peripheral upstanding wall to surround and retain a respective supported end of said cage to prevent lateral cage movement or cage rotation.

25. The spinal replacement device of claim 24 in which said first and second transverse plates are connected to said vertebral attachment plate at opposed edges of said vertebral attachment plate.

26. The spinal replacement device of claim 24 in which a cover member covers a portion of said vertebral attachment plate adjacent the ends thereof on a side opposed to said transverse plates, said cover member being secured to at least one of said transverse plates, whereby said transverse plate and secured cover member can be moved along said vertebral attachment plate to a desired position and then secured in place by tight retention.

27. The spinal replacement device of claim 26 in which said cage comprises a bone having ends of non-circular cross section and a lumen extending therethrough from end to end.

28. The spinal replacement device of claim 27 in which said first and second transverse plates are connected to said vertebral attachment plate at opposed edges of said vertebral attachment plate.

29. The spinal replacement device of claim 24 in which each transverse plate defines a central aperture.

30. An implantable spinal vertebral replacement device, which comprises: a tubular cage for fitting into a space of a missing or damaged vertebral body, and separate first and second transverse plates respectively positioned at opposed ends of the tubular cage supporting the respective cage ends, and for pressing a plate face against an adjacent vertebral body in spinal column-supporting relation, said transverse plates each being each joined in transverse relation to at least one vertebral attachment plate which, in use, extends generally parallel to the spine, said vertebral attachment plate defining screw holes for screw securance to at least one vertebral body adjacent to said space, said transverse plates each having a peripheral, upstanding wall to at least partially surround and retain a respective, supported end of said cage to prevent lateral cage movement and cage rotation, said peripheral, upstanding wall and cage being dimensioned to cause tight retention of said cage, said wall being open at one lateral end of said transverse plate to receive said cage with lateral motion relative to the spinal column.

* * * * *

UNITED STATES PATENT AND TRADEMARK OFFICE
CERTIFICATE OF CORRECTION

PATENT NO.    : 6,395,030 B1                                                Page 1 of 1
DATED         : May 28, 2002
INVENTOR(S)   : Matthew N. Songer et al.

It is certified that error appears in the above-identified patent and that said Letters Patent is hereby corrected as shown below:

<u>Column 8,</u>
Line 46, add claim 31,
      -- 31. An implantable, spinal vertebral replacement device, which comprises:
      a tubular cage for fitting into a space of a missing or damaged vertebral body; and first and second transverse plates respectively positioned at opposed ends of the tubular cage for supporting the respective cage ends and for pressing a plate face against an adjacent vertebral body in spinal column-supporting relation, said transverse plates each defining a central aperture, said transverse plates each being joined in transverse relation to a single vertebral attachment plate, said vertebral attachment plate having screw holes for attachment to a pair of said adjacent vertebral bodies, said vertebral attachment plate, in use, extending generally parallel to the spine for screw securance to the pair of vertebral bodies adjacent to said space, a central, open space extending between the apertures of said first and second plates and through said cage to facilitate bone growth between said adjacent vertebral bodies through said cage. --

Signed and Sealed this

Twenty-second Day of October, 2002

*Attest:*

*Attesting Officer*

JAMES E. ROGAN
*Director of the United States Patent and Trademark Office*